United States Patent [19]
Cole et al.

[11] Patent Number: 5,089,606
[45] Date of Patent: * Feb. 18, 1992

[54] WATER-INSOLUBLE POLYSACCHARIDE HYDROGEL FOAM FOR MEDICAL APPLICATIONS

[75] Inventors: Susan M. Cole, Minneapolis; James E. Garbe, Inver Grove Heights; Lewis P. Woodson, Eagan, all of Minn.

[73] Assignee: Minnesota Mining and Manufacturing Company, St. Paul, Minn.

[*] Notice: The portion of the term of this patent subsequent to Aug. 14, 2007 has been disclaimed.

[21] Appl. No.: 566,269

[22] Filed: Aug. 13, 1990

Related U.S. Application Data

[63] Continuation-in-part of Ser. No. 301,164, Jan. 24, 1989, and Ser. No. 301,312, Jan. 24, 1989, Pat. No. 4,948,575.

[51] Int. Cl.⁵ ............... A61M 5/08; A61L 15/42; A61L 25/00; A61K 31/715
[52] U.S. Cl. .................... 536/54; 604/85; 424/44; 424/445
[58] Field of Search ............ 536/54; 424/44, 445; 604/85

[56] References Cited

U.S. PATENT DOCUMENTS

| | | | |
|---|---|---|---|
| 1,365,183 | 1/1921 | Moffatt | 604/85 |
| 2,441,729 | 5/1948 | Steiner | 99/131 |
| 2,756,874 | 7/1955 | Erickson et al. | 206/47 |
| 2,918,375 | 12/1959 | Gibsen | 99/131 |
| 3,455,701 | 7/1969 | Miller et al. | 99/131 |
| 4,187,286 | 2/1980 | Marcus | 424/44 |
| 4,322,399 | 3/1982 | Ahmad et al. | 424/44 |
| 4,360,013 | 11/1982 | Barrows | 128/130 |
| 4,381,947 | 5/1983 | Fellico | 106/38.5 |
| 4,391,799 | 7/1983 | Mason, Jr. et al. | 424/132 |
| 4,393,048 | 7/1983 | Mason, Jr. et al. | 424/132 |
| 4,401,456 | 8/1983 | Connick, Jr. | 71/88 |
| 4,432,756 | 2/1984 | Urquhart et al. | 604/85 |
| 4,538,918 | 9/1985 | Mittleman | 604/85 |
| 4,538,920 | 9/1985 | Drake | 366/177 |
| 4,613,497 | 9/1986 | Chavkin | 424/44 |
| 4,834,714 | 5/1989 | Lascar et al. | 604/85 |
| 4,948,575 | 8/1990 | Cole et al. | 424/44 |

FOREIGN PATENT DOCUMENTS

| | | |
|---|---|---|
| 368694 | 7/1980 | Fed. Rep. of Germany. |
| 3601132 | 1/1986 | Fed. Rep. of Germany. |
| 424956 | 8/1982 | Sweden. |
| 1579324 | 2/1976 | United Kingdom. |
| 2182663 | 5/1987 | United Kingdom. |

OTHER PUBLICATIONS

Stockwell et al., "In Vitro Evaluation of Alginatee Gel Systems as Sustained Release Drug Delivery Systems", *Journal of Controlled Release*, vol. 3, pp. 167-175 (1986).
Ledger et al., "Prophylactic Cephaloridine in the Prevention of Postoperative Pelvic Infections in Premenopausal Women Undergoing Vaginal Hysterectomy", *Am. J. Obstet. Gynecol.*, vol. 115, pp. 766-774 (1973).
Richardson et al., "Abdominal Hysterectomy: Relationship Between Morbidity and Surgical Technique", *Am. J. Obstet. Gynecol.*, vol. 115, pp. 953-961 (1973).
Pelaez et al., "Improved Method for Preparation of Fruit-Simulating Alginate Gels", *Journal of Food Processing and Preservation*, vol. 5, pp. 63-81 (1981).
Chemical Abstract No. 28563y, vol. 83, No. 3, p. 547 (1975).

*Primary Examiner*—Ronald W. Griffin
*Attorney, Agent, or Firm*—Gary L. Griswold; Walter N. Kirn; Jennie G. Boeder

[57] ABSTRACT

A water-insoluble polysaccharide hydrogel foam and a method and article of preparing a homogeneously foamed hydrogel from a two component aqueous system of water-soluble polysaccharides bearing pendant carboxylate groups. The hydrogel foam, when it incorporates an antimicrobial, has particular utility as a surgical preparation for vaginal or rectal surgery.

25 Claims, 1 Drawing Sheet

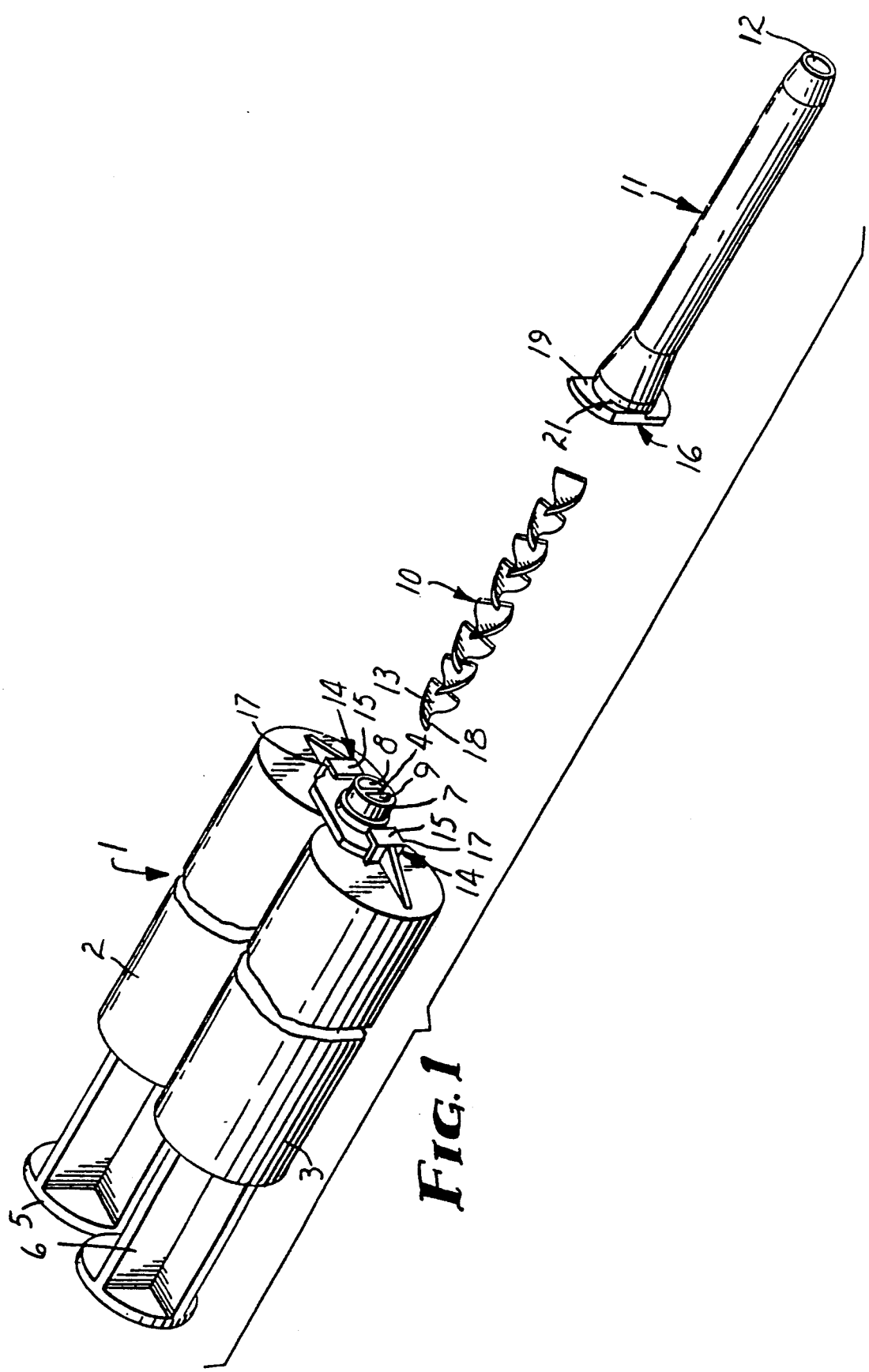

WATER-INSOLUBLE POLYSACCHARIDE HYDROGEL FOAM FOR MEDICAL APPLICATIONS

This application is a continuation-in-part of U.S. Ser. No. 301,164 filed Jan. 24, 1989, and U.S. Ser. No. 301,312, filed Jan. 24, 1989, now U.S. Pat. No. 4,948,575.

TECHNICAL FIELD

This invention relates to the preparation of a waterinsoluble polysaccharide hydrogel foam, and in particular to a process and article useful for preparing the foamed hydrogel from a two component aqueous system. The hydrogel foam, when it incorporates an antimicrobial, has particular utility as a surgical preparation for vaginal or rectal surgery.

BACKGROUND ART

Gels formed by crosslinking polysaccharides bearing pendant carboxylate groups have been known and used for many years in the areas of dental health care and food preparation technologies. Of these gels, the most commonly encountered are composed of water-insoluble alginates which include, with the exception of magnesium and the alkali metal salts, the group II metal salts of alginic acid. These water-insoluble alginate gels are typically formed by the chemical conversion of watersoluble alginates, in an aqueous solution, into waterinsoluble alginates. This conversion usually is accomplished by the reaction of a water-soluble alginate with polyvalent cations released from a soluble di- or trivalent metal salt. The water-soluble alginates include the ammonium, magnesium, potassium, sodium, and other alkali metal salts of alginic acid.

The most common of the alginate gels is composed of calcium alginate Sources for the crosslinking calcium ions used in the formation of these gels generally include calcium carbonate, calcium sulfate, calcium chloride, calcium phosphate, and calcium tartrate Controlling the time of gelatin has traditionally been an integral part of conventional methods of preparing these calcium alginate gels and is usually accomplished by regulating the concentration of free calcium ions in the solution Typically the concentration of free calcium ions is controlled by manipulation of the ionization rate of the calcium salt and/or by the inclusion of other compounds in the solution which react with the free calcium ions.

Conventional processes regulate the rate of ionization by selecting a calcium salt having the desired solubility and/or by adjusting the pH of the solution to increase the solubility of the calcium salt. The solubility of slightly soluble or water-insoluble calcium salts can be increased by lowering the pH of the solution. Generally the pH is lowered by the addition of an acid or by the addition of a substance such as an acid lactone that hydrolyzes to an acid. Commonly used pH adjusters include glucono-delta-lactone and acids such as acetic, adipic, citric, fumaric, lactic and tartaric acid.

The availability of calcium ions can also be controlled by the addition of gel retarders. Known gel retarders are salts having an ion that forms a water-insoluble or slightly water-soluble bond to the calcium ions. The retarder competes with the water-soluble alginate for the free calcium ions thereby depriving the alginate of some of the crosslinking ions and delaying gelatin Common retarders are the alkali metal phosphates, oxalates and citrates.

Conventional methods for preparing these waterinsoluble calcium alginate gels typically involve adding solid water-soluble alginate and solid calcium salt to an aqueous medium as disclosed in U.S. Pat. No. 3,455,701, and U.K. Patent Specification No. 1,579,324, published Nov. 19, 1980, or adding a solution or dispersion of calcium salt to an aqueous solution of water-soluble alginate as disclosed in U.S. Pat. Nos. 2,756,874, 4,381,947 and 4,401,456. Typically these methods include the addition of gel retarders and/or pH adjusters to provide control over the rate of gelatin.

Traditionally, water-insoluble alginate gels have been used extensively in dental impression materials and as thickening or setting agents in food preparations Recently, however, water-insoluble alginate gels have found utility as a form-in-place wound dressing material as disclosed in Swedish Patent Application Publication No. 424,956, published Aug. 23, 1982. This dressing is prepared by mixing water-soluble alginate, a soluble metal salt having metal ions that react with the watersoluble alginate to form a crosslinked water-insoluble alginate, and water to form a reactive cream-like paste that is spread over the wound surface After application to the wound surface the constant progression of the crosslinking reaction transforms the cream-like paste into an elastic rubber-like composition.

Likewise, German Patent Application No. 3601132 (published July 23, 1987), discloses an alginate which gels in situ and is useful for protecting the mucosa and delivering disinfectants or pharmaceutically active agents. The composition consists of at least two components capable of forming a gel on mixing, such as a calcium salt and alginic acid, polyglucuronic acid, polymanuronic acid, propylene glycol alginic acid, polygalacturonic acid, polyarabinic acid, their salts or esters, pectin, gum arabic and their mixtures, to be simultaneously or sequentially placed onto the mucous membrane.

Alginate gels have also been used to provide sustained release of drugs. Stockwell, et al., in "In Vitro Evaluation of Alginate Gel Systems as Sustained Release Drug Delivery Systems", *Journal of Controlled Release*, Volume 3, pp. 167–175 (1986), disclose gelatin capsules containing a powdered mixture of sodium alginate, calcium phosphate, sodium bicarbonate, lactose and a drug (chlorpheniramine, sodium salicylate or caffeine). In situ in the stomach the gelatin capsule dissolves, hydration and gelatin of the alginate and crosslinking by calcium occur to provide a gel barrier at the surface, and the sodium bicarbonate effervesces, releasing carbon dioxide which becomes entrapped in the gel network.

Another sustained release device is disclosed in U.S. Pat. No. 4,613,497. Anhydrous tablets, capsules, powders or suppositories are made from a mixture of water soluble polysaccharide gum, a biocompatible gelling salt, an effervescent base, a water soluble biocompatible acid or acid salt and a pharmaceuticaly active material. These compositions find use in gastrically active compositions and vaginal contraceptives.

Furthermore, German Patent No. 368,694 discloses a foaming dental adhesive made from an adhesive material, such as alginic acid or sodium alginate, at least one carbonate and/or hydrogen carbonate and at least one organic, water-soluble salt or a water-soluble acid salt of a polyboric acid. The later two components form $CO_2$ in an aqueous environment and stimulate foaming of the adhesive.

Medical uses for these gels brings with it new concerns with regard to the purity and sterility of the polysaccharide gel being formed. For example, it is generally desirable that retarders and suspending agents which leave residual deposits in the gel network not be present in the gel forming components used to form foamed polysaccharide hydrogels for medical uses Furthermore, to be effective in preventing contamination and infection, it is generally desirable that the hydrogel forming materials be sterile prior to their application.

Theoretically, a sterile form-in-place polysaccharide hydrogel may be prepared by either (1) sterilizing the gel-forming components separately prior to mixing and maintaining the components in a sterile environment before, during and after mixing until the composite material is used, or (2) mixing the gel-forming components together first and then sterilizing the composite material immediately prior to use. The latter alternative, however, has little practical utility as it requires each batch to be individually sterilized prior to use, and thereby places unacceptable demands upon the time and facilities of the health care professional. Likewise, in order for the former alternative to be useful, sterile gel-forming components, and a method of mixing these components while maintaining them in a sterile environment, must be available to the health care professional.

Thus, there is a need in the medical arts for a foam-in-place polysaccharide hydrogel which can be easily provided in a sterile form. Additionally, it is desirable for the gel-forming components to mix easily and quickly so as to minimize the demands on the health care professional's time and energy. It is further desirable to provide a foam forming mechanism which coordinates the rate of gel formation with the rate of foam formation, so as to assure uniform dispersal of foam within the gelled polysaccharide structure. Only in this way can a dimensionally stable foamed polysaccharide hydrogel be produced.

Heretofore it has been unknown to employ polysaccharide hydrogels as preoperative preparations. There exists a need for an effective form-in-place surgical preparation, particularly one well suited for vaginal or rectal surgery. Nosocomial infections are more common after vaginal or rectal surgery largely because the surgical techniques are done through an already contaminated field. Attempts to reduce infections have been made using prophylactic antibiotics, (Ledger WJ, Sweet RI, Headington JT: "Prophylactic Cephaloridine in the Prevention of Post-Operative Infection in Premenopausal Women Undergoing Vaginal Hysterectomy." *Am. J. Obstet Gynecol.* 1973:115-766), various preoperative preparations (Telinde R: Operative Gynecology. Philadelphia, JB Lippincott Co., 1962, p.8.), different surgical techniques (Richardson AC, Lyon JB, Graham EE: "Abdominal Hysterectomy: Relationship Between Mortality and Surgical Technique." *Am. J. Obstet. Gynecol.* 115:953-961 (1973)), and specific drainage systems (Swartz WH, Tanaree P: "T-tube Suction Drainage and/or Prophylactic Antibiotics: Randomized Study of 451 Hysterectomies". *Obstet Gynecol.* 47:665-670 (1976)) with no significant decrease.

Because none of these methods has been successful in decreasing infection following vaginal and/or rectal surgical procedures, there remains a need for a surgical preparation that 1) is capable of releasing antimicrobial in a prolonged manner for up to 24 hours or more; 2) swells to the shape of the cavity into which it is injected, thus delivering antimicrobial to a large surface area; 3) forms a stable, biocompatible, water-insoluble gel that will absorb exudates with very little swelling; and 4) can be easily removed from the body cavity as a complete unit.

SUMMARY OF THE INVENTION

The present invention provides a water-insoluble polysaccharide hydrogel foam which is prepared from an aqueous two component mixture. One component, Component A, comprises an aqueous suspension of certain water-insoluble di- or trivalent metal salts and an effervescent compound. The other component, Component B, comprises an aqueous solution of a water-soluble acid. At least one component, and preferably both, contain a water-soluble polysaccharide bearing pendant carboxylate groups. Optionally, for medical applications, at least one component, and preferably both, include a medicament.

The water-insoluble polysaccharide hydrogel foam formed from the two-component aqueous system of the present invention comprises a) about 0.02 to 60 percent by weight of one or more polysaccharides complexed with a di-or trivalent metal salt; b) the gaseous reaction product of an effervescent compound and a water-soluble acid in a concentration sufficient to provide the cured hydrogel foam with a density of from about 0.1 to 1 $g/cm^3$; c) from about 50 to 98 percent by weight of an aqueous medium; and d) optionally, for medical applications, about 0.001 to 10 percent by weight of a medicament.

The present invention further provides a preoperative preparation which is particularly useful for vaginal or rectal surgery. The preoperative preparation is formed in situ by applying a reactive gel-forming composition directly to the operative site. The reactive gel-forming composition comprises: (a) an aqueous solution of a water-soluble polysaccharide which bears pendant carboxylate groups, (b) a water-soluble acid dissolved therein, (c) particles of a water-insoluble di-or trivalent metal salt that will react with an acid to form a water-soluble metal salt, and which has a di- or trivalent metal ion capable of complexing with the pendant carboxylate groups of said water-soluble polysaccharide to form a water-insoluble polysaccharide hydrogel, suspended therein, (d) an effervescent compound which effervesces upon reaction with an acid, and e) a medicament. The reactive composition can be dispensed into a body cavity and will form a stable medicated water-insoluble polysaccharide hydrogel foam which exactly fits the shape and contour of the cavity within about 1 to 8 minutes. The medicated foam can provide prolonged release of the medicament in the body cavity for up to 24 hours or more. The medicated polysaccharide hydrogel foam prepared according to the invention is bio-compatible and dimensionally stable. It is capable of absorbing exudates from the body cavity without any appreciable swelling. The hydrogel foam remains moist, thereby reducing trauma and irritation to the surrounding tissue, but has sufficient structural integrity to be removed from the body cavity in one piece, even though it may be saturated with body fluids or other aqueous fluids.

While the medicated water-insoluble polysaccharide hydrogel foams of the invention have particular utility as a preoperative preparation for the vaginal and/or rectal cavity to provide an improved aseptic environment, they also have utility as medicament(s) dispensing devices for any body cavity or surface. For example, they may be used as wound dressings, sustained release drugs or vaginal contraceptives.

Additionally, the present invention provides a self-contained device ideally suited for the preparation and delivery of a sterile medicated water-insoluble polysaccharide hydrogel foam. The device comprises a first chamber containing a first liquid component comprising an aqueous suspension of a water-insoluble di-or trivalent metal salt and a substance which effervesces upon reaction with an acid; a second chamber containing a second liquid component comprising an aqueous solution of a biocompatible water-soluble acid, wherein either or both the first or second liquid components further comprise a water-soluble polysaccharide having pendant carboxylate groups and a medicament dissolved or suspended therein; and a means connected to the first and second chambers for allowing intermixing of the first and second liquid components.

BRIEF DESCRIPTION OF DRAWING

A preferred embodiment of the invention is illustrated in the accompanying drawing, in which:

FIG. 1 is an exploded view in perspective of a double-barreled syringe, static mixing element, and mixing tip with outlet of the device of this invention.

DETAILED DESCRIPTION OF THE INVENTION

The invention provides a homogeneous water-insoluble polysaccharide hydrogel foam composed of one or more water-insoluble polysaccharides complexed with salts which include (with the exception of magnesium) the alkaline earth metal salts and the group III metal salts. The homogeneous polysaccharide hydrogel foam is formed by mixing together a first liquid component (Component A) comprising an aqueous suspension of particles of a water-insoluble di- or trivalent metal salt, and an effervescent compound which effervesces upon reaction with an acid; and a second liquid component (Component B) comprising an aqueous solution of a water-soluble acid; wherein at least one of Components A and B further comprises a water-soluble polysaccharide having pendant carboxylate groups. It is preferred that the water-soluble polysaccharide be dissolved in Component A, and more preferred that the water-soluble polysaccharide be dissolved in both Component A and Component B. It is further preferred for medical applications, that a medicament be dissolved or suspended in both Component A and Component B, and more preferred that it be dissolved or suspended in Component A.

Upon mixing Components A and B, the water-insoluble metal salt reacts with the water-soluble acid to form a water-soluble metal salt that is subsequently ionized. The polyvalent cations released from the water-soluble metal salt complex with the pendant carboxylate groups of the water-soluble polysaccharide causing the formation and precipitation of a water-insoluble polysaccharide hydrogel. At the same time, the effervescent compound is reacting with the water-soluble acid with the resultant evolution of gases which become entrapped in the forming gel network, causing the formation of a stable hydrogel foam.

The polysaccharides useful in the present invention are biocompatible, water-soluble, have pendant carboxylate groups, and complex with polyvalent cations to form hydrogels. Suitable polysaccharides include the water-soluble salts of alginic, pectic and hyaluronic acids; the water-soluble salts or esters of polyglucuronic acid, polymanuronic acid, polylygalacturonic acid and polyarabinic acid; and gum kappa-carrageenan. The preferred polysaccharides are the ammonium, magnesium, potassium, sodium and other alkali metal salts of alginic acid, and the most preferred polysaccharide is sodium alginate.

Alginate is the general name given to alginic acid and its salts. Alginates are composed of D-mannosyluronic (mannuronic) and L-gulopyranosyluronic (guluronic) acid residues. The ratio between mannuronic/guluronic acid affects the properties of the alginates. Alginates high in mannuronic acid are best suited for thickening applications, whereas alginates with a high level of guluronic acid are best for forming gels. For this invention it is preferred that the alginate have a high level of guluronic acid, i.e., greater than about 50 percent by weight. For example alginates from the algae Laminaria lyperburea, stem, whole plant or frond, have a high level of guluronic acid and are particularly preferred.

The water-insoluble di- or trivalent metal salts useful in the present invention must satisfy two requirements. First, the water-insoluble metal salt must contain a di-or trivalent metal ion capable of complexing with the pendant carboxylate groups of the water-soluble polysaccharide to cause the formation of a water-insoluble polysaccharide gel. Second, the water-insoluble metal salt must react with a water-soluble acid to form a water-soluble metal salt. Preferred water-insoluble metal salts useful in the present invention include calcium carbonate, calcium phosphate dibasic ($CaHPO_4$), barium carbonate and zinc carbonate, with calcium carbonate being the most preferred.

The water-soluble acids useful in the present invention may be chosen from monocarboxylic and polycarboxylic acids. For medical applications, the water-soluble acid must also be biocompatible. Examples of suitable acids include acetic acid, citric acid, tartaric acid, succinic acid, formic acid, glycolic acid, malonic acid, dichloroacetic acid, oxalic acid, lactic acid, malic acid, gluconic acid, adipic acid, fumaric acid, alginic acid and maleic acid. The most preferred water-soluble acid is acetic acid.

The effervescent compound used in the present invention must effervesce upon reaction with the water-soluble acid. Useful effervescent compounds may be chosen from the alkali metal carbonates or bicarbonates, such as sodium bicarbonate, sodium carbonate, calcium carbonate and potassium carbonate. The most preferred effervescent compound is sodium carbonate.

Although recited as separate elements of Component A, it should be understood that in some cases the water-insoluble di- or trivalent metal salt and the effervescent compound may both be provided by a single compound. For example, the preferred water-insoluble metal salt, calcium carbonate, releases carbon dioxide gas upon reaction with the acid in Component B and, thus, produces a hydrogel foam without the inclusion of any other effervescent compounds. The resultant foam, however, generally has a relatively high density and low void volume due to the small amount of carbon dioxide typically produced by this reaction. Thus, even if the water-insoluble di- or trivalent metal salt effervesces, it may still be desirable to include an additional effervescent compound in order to obtain a hydrogel foam having a greater void volume and lower density.

The medicament useful in the present invention is chosen from any physiologically or pharmacologically active substance that produces a local or systemic effect when released in a biological environment. The active medicament can be inorganic or organic compounds including drugs that act on the nervous system; drugs that act on tissues, muscles, and organs; analgesics; anti-inflammatory agents; prostaglandins; antimicrobials; anti-virals; antifungal agents; and hormones Resources for beneficial drugs and doses are REMINGTON'S PHARMACEUTICAL SCIENCES, 14th Edition, 1970; Mack Publishing Co., Easton, PA.; and Goodman and Gilman, THE PHARMACOLOGICAL BASIS OF THERAPEUTICS, 7th Edition, 1985; MacMillian Company, New York, New York; both of which are incorporated herein by reference.

Antimicrobials are the preferred medicament. Three particularly preferred antimicrobials are iodophors, iodine and bacitracin. Preferred iodophors include combinations of elemental iodine with detergent polymers such as nonylphenoxy poly(ethylenoxy) ethanol and undecoylium chloride; or complexes of iodine with a nonionic, non detergent, non-surface active, water-soluble organic polymer, such as polyvinylpyrrolidone (povidone), polydextrose or a copolymer of sucrose and epichlorohydrin. Povidone and polydextrose are particularly preferred nonionic, non-detergent water-soluble polymers U.S. Pat. No. 4,576,818, incorporated herein by reference, describes the preparation of polydextrose iodine from polydextrose and iodine. U.S. Pat. No 2,739,922, incorporated herein by reference, describes the preparation of polyvinylpyrrolidone-iodine from polyvinylpyrrolidone and iodine.

Preferred iodine preparations are in the form of aqueous or alcoholic solutions such as iodine and postassium or sodium iodide in water, ethyl alcohol, and glycerol, or in a mixture of these solvents. The following preparations are preferred: iodine topical solution, an aqueous solution containing 2.0% by wt. iodine and 2.4% by wt. sodium iodide; strong iodine solution, an aqueous solution containing 5% by wt. iodine and 10% by wt. potassium iodide; and iodine tincture in aqueous ethanol (1:1) solution containing 2% by wt. iodine and 2.4% by wt. sodium iodide. The concentration of iodine depends on the germicidal strength required, the propensity of the iodine to cause irritation, and the length of use. The preferred concentration is 0.1 to 5% by weight available iodine and the most preferred concentration is 0.5 to 1.5% by weight available iodine Bacitracin is one or more of the antimicrobial polypeptides produced by certain strains of Bacillus licheniformis and by Bacillus subtilis variety Tracy. It usually contains not less than 55 units per mg calculated with reference to dried substance. The preferred concentration of bacitracin is 250 units/ml to 150,000 units/ml and the most preferred concentration is 5000 units/ml to 50,000 units/ml.

The aqueous medium in which the constituents of Components A and B are carried can comprise any compatible solvent in which the particular components are soluble or dispersible. Preferably, distilled water is employed.

The water-insoluble polysaccharide hydrogel foam of this invention is formed simply by mixing together the first liquid component, Component A, and the second liquid component, Component B, and allowing the reaction mixture to cure to a dimensionally stable homogeneous hydrogel foam. The rate of cure is governed by the rate of the reaction between the water-soluble acid and the water-insoluble metal salt and is thus controlled by the amounts of the metal salt and acid in the solution. The water-insoluble metal salt is present in Component A in a concentration of from about 0.01 to 10.0 percent by weight of Component A, preferably from about 0.5 to 2.0 percent by weight, and most preferably from about 1.0 to 1.5 percent by weight. The water-soluble acid is present in Component B in a concentration of from about 0.01 to 10.0 percent by weight of Component B, preferably from about 1 to 4 percent by weight and most preferably from about 2 to 3 percent by weight. Using the preferred concentration of ingredients, a hydrogel having a cure time of from one to eight minutes can be provided.

The concentrations of the other constituents of Components A and B are as follows. If an effervescent compound, other than the metal salt, is present in Component A, it is present in a concentration of from about 0.01 to 10.0 percent by weight of Component A preferably from about 0.5 to 3 percent by weight, and most preferably from about 1 to 2 percent by weight.

The water-soluble polysaccharide is present in either Component A or Component B in a concentration of from about 0.01 to 50.0 percent by weight of that component. Preferably the polysaccharide is present in both Components A and B in a concentration of about 0.5 to 10.0 percent by weight of each component, most preferably between about 2 and 7 percent by weight of each component.

The medicament concentration is dependent upon the medicament identity and the use intended for the polysaccharide hydrogel foam. For most uses, when the medicament is an antimicrobial, the concentration of medicament present in either Component A or Component B is sufficient to provide the reacted polysaccharide hydrogel foam with from about 0.001 to 10 by weight, preferably from 0.5 to 4.0 by weight medicament.

The aqueous medium which constitutes the remainder of Components A and B, forms from about 50 to 98 percent by weight of each component. Preferably water constitutes about 75 to 97 percent by weight of Component A and Component B. Most preferably water forms about 85 to 95 percent by weight of Component A and about 85 to 95 percent by weight of Component B.

The cured water-insoluble polysaccharide hydrogel foam comprises: polysaccharide complexed with an di- or trivalent metal salt in a concentration of from about 0.02 to 60 percent by weight, preferably from about 1 to 12 percent by weight, and most preferably from about 3 to 8.5 percent by weight of the cured hydrogel foam; the gaseous reaction product of an effervescent compound and a biocompatible, water-soluble acid in a concentration sufficient to provide the cured hydrogel foam with a density of from about 0.1 to 1 g/cm$^3$, preferably about 0.25 to 0.7 g/cm$^3$, and most preferably about 0.35 to 0.5 g/cm$^3$; with the remainder of the cured hydrogel foam comprising the aqueous medium. Preferably the aqueous medium comprises about 50 to 98 percent by weight of the cured foam, most preferably about 85 to 95 percent by weight of the cured foam. Optionally, for medical applications, a medicament is present in a concentration of about 0.001 to 10 percent by weight, preferably about 0.01 to 8 percent by weight, and most preferably about 0.05 to 4 percent by weight of the cured foam.

The medicated water-insoluble polysaccharide hydrogel foam of this invention is formed in place in, for example, the vaginal or rectal cavity, simply by mixing Component A with Component B and applying the reactive composite mixture directly into the body cavity. The reaction mixture swells and cures to a homogeneous, dimensionally stable polysaccharide hydrogel in normally 2 to 3 minutes. The cured hydrogel exactly fits the cavity or surface to which it is applied, enabling medication to be delivered evenly through a prolonged release mode.

While the medicated polysaccharide hydrogel foams of this invention are particularly useful as preoperative preparations for vaginal or rectal surgery, to minimize contaminations preoperatively and thus infections postoperatively, they also find use as medicament(s) dispensing devices for body cavities or surfaces. A preferred use of the medicated hydrogel foam is as a suppository for the delivery of medicament.

In practice, the water-insoluble polysaccharide hydrogel foam can be prepared and applied using a self-contained article comprising a first chamber containing Component A, a second chamber containing Component B, and a means connected to said first and second chambers for intermixing Components A and B without exposing them to the atmosphere or to any external mixing devices One example of such an article is a closed bag divided into two compartments by a removable closure, with Component A contained within the compartment on one side of the closure and Component B contained within the compartment on the opposite side of the closure. In this embodiment of the article, mixing of the two components can be accomplished simply by removing the closure and manually forcing the two components together.

Another example of such an article comprises two permanently separated component-containing chambers wherein each component-containing chamber is equipped with a discharge opening leading to a common mixing chamber. In this embodiment of the article, mixing of the two components can be accomplished by forcing each of the components from their respective chambers into the mixing chamber. Preferably the mixing chamber is in the form of a baffled discharge tube so that the components are mixed as they are discharged from the article through the discharge tube. A useful example of such an article is a double-barreled syringe assembly equipped with a standard mixing tip. Such an article is illustrated in FIG. 1.

Referring now to FIG. 1, there is shown an exploded view in perspective of a preferred embodiment of the device of this invention. Syringe 1 has two parallel internal chambers, 2 and 3, each of which is intended to be filled with Component A or Component B. The chambers 2 and 3 in syringe 1 are separated by barrier 4. When plungers 5 and 6 are forced into chambers 2 and 3, respectively, the contents of the syringe exit via outlet 7. The contents of chamber 2 exit outlet 7 by flowing through outlet passage 8. The contents of chamber 3 exit outlet 7 by flowing through outlet passage 9. The contents of both chambers 2 and 3 are intimately mixed by static mixing element 10 to form a homogeneous mass in mixing tip 11. The homogeneous mass rapidly reacts to form a stable foam following expulsion from outlet 12 of mixing tip 11. Static mixing element 10 is prevented from being expelled during use from the outlet end 12 of mixing tip 11 by a suitable constriction in the inside diameter of tip 11 proximate outlet end 12.

Mixing element 10 comprises multiple counter-rotated auger-like mixing blades 13. Preferably, the inlet end 18 of static mixing element 10 is aligned generally perpendicular to the plane of contiguity between the two streams exiting syringe 1 through exit passages 8 and 9. Means of accomplishing r this orientation are described in U.S. Pat. No. 4,538,920, incorporated herein by reference.

Attachment of mixing tip 11 to syringe 1 is achieved by a suitable mounting means (e.g., a bayonet mount). Bayonet locking tabs 14 have locking prongs 15 and step surfaces 17. Mixing tip 11 has locking ramps 19 and step surfaces 21. Mixing tip 11 is mounted on syringe 1 by centering the inlet 16 of mixing tip 11 over outlet 7 of syringe 1, while aligning mixing tip 11 so that it can be pushed between bayonet locking tabs 14. Mixing tip 11 is then inserted firmly over outlet 7, and rotated approximately 90° clockwise (as viewed from the outlet 12 of the mixing tip) so that the locking ramps 19 are wedged between locking prongs 15 and the main body of syringe 1, and stop surfaces 17 engage stop surfaces 21. Static mixing element 10 and mixing tip 11 are firmly attached to syringe 1, but can be readily removed and discarded after use by rotating mixing tip 11 approximately 90° counterclockwise (as viewed from the outlet 12 of the mixing tip) and pulling mixing tip 11 away from syringe 1.

A preferred self-contained article for preparing and applying the polysaccharide hydrogel foam of this invention is disclosed in U.S. Pat. No. 4,538,920, incorporated herein by reference. A preferred dispenser device for causing the plungers 5 and 6 to move within the chambers 2 and 3 is the 3M "Express Dispenser" commercially available from 3M St. Paul, Minnesota.

The invention is further illustrated by the following non-limiting examples wherein all percentages are by weight unless otherwise specified.

EXAMPLE 1

PREPARATION OF A SLIGHTLY FOAMED ALGINATE GEL

A suspension of calcium carbonate ($CaCO_3$) in an aqueous solution of sodium alginate was prepared by adding 0.21 g solid $CaCO_3$ to 38.6 g of a 4.5% aqueous sodium alginate solution.

An aqueous sodium alginate solution containing enough acetic acid to react with all of the CaCO: was prepared by adding 0.35 g of a 50% aqueous acetic acid solution to 37.66 g of a 4.5% aqueous sodium alginate solution.

The two alginate solutions were loaded into a double-barreled syringe assembly fitted with a 12-element mixing tip. The two solutions mixed as they were discharged through the tip and formed a slightly foamed homogeneous gel in approximately one minute.

EXAMPLE 2

PREPARATION OF A HIGHLY FOAMED ALGINATE GEL

A suspension of calcium carbonate ($CaCO_3$) and sodium carbonate ($Na_2CO_3$) in an aqueous sodium alginate solution was prepared by adding 0.41 g $CaCO_3$ and 0.83 g $Na_2CO_3$ to 36.64 g of a 4.5% aqueous sodium alginate solution.

An aqueous sodium alginate solution containing acetic acid was prepared by adding 1.4 g of a 50% aqueous acetic acid solution to 37.0 g of a 4.5% aqueous sodium alginate solution.

The two alginate solutions were mixed via the double-barreled syringe assembly of Example 1. Foaming began immediately upon mixing and a stable highly foamed homogeneous gel formed in approximately two minutes.

EXAMPLE 3

An alginate hydrogel foam containing iodine was prepared as follows:

1. Component A was prepared by mixing 2.2 g of sodium alginate commercially available as "Protanal LF 20/60 Sodium Alginate" from Protan Inc. of North Hampton, New Hampshire, with 0.90 g of sodium carbonate and 38.4 g of deionized water, at room temperature. The mixture was stirred until completely homogenous. Then 0.90 g of calcium carbonate was added.
2. Component B was prepared by mixing 0.42 g of sodium iodide and 0.42 g of iodine with 37.68 g of deionized water at room temperature. The mixture was stirred until the iodide and iodine were completely dissolved. Then 2.2 g of glacial acetic acid was added. Next 2.2 g of the same sodium alginate used in the preparation of Component A was added and the mixture stirred until the alginate was completely dissolved.
3. Components A and B were loaded, in equal volumes, into separate barrels of a double-barreled mixing syringe assembly fitted with a 3-inch, 6-turn mixing tip and
4. Components A and B were discharged through the mixing tip of the mixing syringe into a 50 ml conical tube and allowed to foam and cure for 3 minutes.

EXAMPLES 4-11

Medicated alginate hydrogel foams were prepared by the same method and from the same reactants used in the preparation of the alginate hydrogel foam of Example 3. The preparation of the alginate hydrogel foams of Examples differs from the preparation of the foam of Example 3 only in the ratios of the iodine/sodium iodide (%wt/v) used. The ratios of iodine/sodium iodide (%wt/v) used to prepare the foams of Examples 4-11 are shown in Tables I and II.

The bacteriostatic and bacteriocidal capabilities of the medicated hydrogel foams were measured by determining the Zone of Inhibition of microorganism growth in agar. The microorganism $Log_{10}$ reduction method was used to determine the effectiveness of the medicated hydrogel foam for eliminating the microbial flora commonly found in an operative field.

(A) Zone of Inhibition

As in Example 3, Component A and Component B were mixed and allowed to cure in a 50 ml conical tube. A 1.5 g disk, 28 mm in diameter, was cut out of each cured hydrogel foam and aseptically placed in a petri dish on solidified nutrient agar, commercially available from Difco Laboratory, Inc., Detroit, MI. Sterile nutrient agar at 43° C. was inoculated with *Staphyloccus epidermidis* (ATCC #12228), *Pseudomonas aeruginosa* (ATCC #15422), or *Escherichia coli* (ATCC #15221) obtained from log phase overnight cultures grown in nutrient media commercially available as "rypticase Soy Broth" from Difco Laboratory, Inc. Detroit, MI at 36° C. Ten ml of the inoculated agar was poured onto the agar in the petri dish containing the hydrogel foam and the inoculated agar was allowed to solidify at room temperature. The petri dish with inoculated agar and hydrogel foam disk was incubated overnight at 36° C. The Zone of Inhibition was determined by measurement of diameter of the disk without microorganism growth. The following code was used:

| Zone Diameter | Zone Results |
| --- | --- |
| 20-greater mm | + + + + + |
| 15-20 mm | + + + + |
| 10-15 mm | + + + |
| 5-10 mm | + + |
| 0-05 mm | + |

The results are shown in Table I and indicate that increasing the ratio of iodine/sodium iodide (%wt/v) in the medicated foam causes a steady increase in the Zone of Inhibition.

TABLE I

| Ex. No. | Iodine/Sodium Iodide (% wt/v) | Zone of Inhibition | | |
| --- | --- | --- | --- | --- |
| | | S. epid | E. coli | P. aerug |
| 4 | 0.25 | + | + | + |
| 5 | 0.50 | + + | + + | + + |
| 6 | 0.75 | + + | + + | + + |
| 7 | 1.00 | + + + | + + + | + + + |
| 8 | 1.25 | + + + | + + + | + + + |
| 9 | 1.50 | + + + + | + + + + | + + + + |
| 10 | 1.75 | + + + + + | + + + + + | + + + + + |
| 11 | 2.00 | + + + + + | + + + + + | + + + + + |

(B) Microorganism $Log_{10}$ Reduction

Microorganism loaded membrane filters were prepared by:
(1) growing cultures overnight of each of the following: *Staphyloccus epidermidis* (ATCC #1228), *Pseudomonas aeruginosa* (ATCC #15422), and *Escherichia coli* (ATCC #15221) in nutrient media commercially available as "Trypticase Soy Broth" from Difco Laboratories, Detroit, MI, at 36° C.;
(2) centrifuging each culture at 2700 rpms for 30 minutes at 4° C.;
(3) resuspending the microorganisms in a sterile saline solution (0.85% wt/v) to an optical density of 0.4 at 660 nm with a 1.5 cm light path;
(4) loading each suspension in a 3 cc disposable syringe equipped with a 3.81 cm (1.5 inch), 22 gauge needle; and
(5) evenly dispersing a 2.0 ml volume of each suspension onto an analytical membrane filter, commercially available as "Falcon 7103, Disposable Sterile Filter Unit" from Fisher Scientific, Pittsburgh, PA. The filter matrix is cellulose nitrate, 5 cm in diameter with a pore size of 0.22 microns.

Upon each microorganism loaded membrane filter, 22.3 g of Component A and 22.3 g of Component B (as described in Example 3) were dispensed and allowed to foam and gel for 3 minutes.

The filter unit was briefly evacuated with a cold water aspirator to a vacuum of 29 inches of Hg, for 10-15 seconds, placed on a clean bench, and covered ajar for 3.5 minutes of incubation at room temperature. The filter was harvested by unlocking the unit and aseptically transferring the intact membrane to 100 ml of sterile saline solution containing 0.1% (wt/v) sodium thiosulfate and 0.1% (wt/v) sodium benzoate contained in a glass Waring Blender jar. Each filter was thoroughly disintegrated by a 5 minute high-speed agitation to enhance recovery of viable microorganisms and to neutralize residual antimicrobial agents. A 2 ml aliquot was removed from the homogenized suspension for a viability count. Duplicate agar plates were prepared from 1 ml of undiluted aliquot and the following aliquot dilutions: $10^{-1}$, $10^{-2}$, $10^{-3}$, $10^{-4}$, and $10^{-5}$. The plates were incubated overnight at 36° C., or longer if necessary, to allow automated counting with the "Biotran II Automated Colony Counter" commercially available from New Brunswick Scientific Co., Inc., Edison, N.J. An average number of colonies was determined by counting each of the duplicate plates four times and taking the average. The same process was repeated on loaded membrane filters which were not treated with medicated foam. The $Log_{10}$ Reduction achieved with the medicated foam was determined by subtracting the $Log_{10}$ of the average number of colonies on the plates prepared using the medicated foam from the $Log_{10}$ of the average number of colonies on the plates prepared without using the medicated foam. The results are shown in Table II.

TABLE II

| Ex No. | Iodine/Sodium Iodide (% wt/v) | $Log_{10}$ Reduction after 3.5 Minutes | | |
|---|---|---|---|---|
| | | S. epid | E. coli | P. aerug |
| 4 | 0.25 | 1.0 | 0.0 | 0.0 |
| 5 | 0.50 | 1.0 | 1.0 | 1.0 |
| 6 | 0.75 | 2.0 | 2.0 | 1.0 |
| 7 | 1.00 | 3.0 | 2.0 | 2.0 |
| 8 | 1.25 | 4.0 | 3.0 | 2.5 |
| 9 | 1.50 | 4.0 | 4.0 | 3.0 |
| 10 | 1.75 | 5.0 | 5.0 | 4.0 |
| 11 | 2.00 | 5.0 | 5.0 | 5.0 |

Increasing the ratio of iodine/sodium iodide (%wt/v) in Component B results in a decrease in the average number of colonies. Table II illustrates that the medicated foam with a ratio of iodine/sodium iodide (%wt/v) of at least 1.00 would be effective for eliminating the microbial flora used in these examples.

EXAMPLE 12

An alginate hydrogel foam containing povidone/iodine was prepared as follows:
1. Component A was prepared by mixing 2.2 g of sodium alginate commercially available as "Protanal LF 20/60 Sodium Alginate" from Protan Inc. of North Hampton, New Hampshire, with 0.90 g of sodium carbonate and 38.4 g of deionized water, at room temperature. The mixture was stirred until completely homogenous. Then 0.90 g of calcium carbonate was added with thorough mixing.
2. Component B was prepared by mixing 4.28 g of povidone and 0.42 g of iodine powder, USP, commercially available from Napp Chemicals, Inc. of Lodi, NJ, with 34.12 g of deionized water at room temperature. The mixture was stirred until completely dissolved. Then 2.2 g of glacial acetic acid was added with thorough mixing. Next 2.2 g of the same sodium alginate used in the preparation of Component A was added and the mixture was stirred until the alginate was completely dissolved.
3. Components A and B were loaded, in equal volumes, into separate barrels of a double-barreled mixing syringe assembly fitted with a 3-inch, 6-turn mixing tip; and
4. Components A and B were discharged through the mixing tip of the mixing syringe into as 50 ml conical tube and allowed to foam and cure for 3 minutes.

EXAMPLES 13-18

Medicated alginate hydrogel foams were prepared by the same method and from the same reactants used in the preparation of the alginate hydrogel foam of Example 12. The preparation of the alginate hydrogel foams of Examples 13-17 differs from the preparation of the foam of Example 12 only in the ratios of povidone/iodine (%wt/v) used. The ratios of povidone/iodione (%wt/v) used to prepare the foams of Examples 13-17 are shown in Tables III and IV.

The bacteriostatic and bacteriocidal capabilities of the medicated hydrogel foams were measured by determining the Zone of Inhibition of microorganism growth in agar as described in Examples 4-11. The results are recorded in Table III.

TABLE III

| Ex. No. | Povidone/Iodine Iodide (% wt/v) | Zone of Inhibition | | |
|---|---|---|---|---|
| | | S. epid | E. coli | P. aerug |
| 13 | 2.0 | + | + | + |
| 14 | 4.0 | + + | + | + |
| 15 | 6.0 | + + | + + | + + |
| 16 | 8.0 | + + + | + + + | + + + |
| 17 | 10.0 | + + + + | + + + + | + + + + |

Increasing the ratio of povidone/iodine (%wt/v) in the medicated foam results in a steady increase in the Zone of Inhibition.

The microorganism $Log_{10}$ reduction method described in Examples 4-11 was used to determine the effectiveness of the medicated hydrogel foams for eliminating microbial flora commonly found in an operative field. The results are recorded in Table IV.

TABLE IV

| Ex. No. | Povidone/Iodine Iodide (% wt/v) | $Log_{10}$ Reduction after 3.5 Minutes | | |
|---|---|---|---|---|
| | | S. epid | E. coli | P. aerug |
| 13 | 2.0 | 0.5 | 0.5 | 0.5 |
| 14 | 4.0 | 1.0 | 1.0 | 1.0 |
| 15 | 6.0 | 1.0 | 1.0 | 1.0 |
| 16 | 8.0 | 2.0 | 2.0 | 2.0 |
| 17 | 10.0 | 3.0 | 3.0 | 3.0 |

Increasing the ratio of povidone/iodine (%wt/v) results in a decrease in the average number of colonies. The medicated foam with a ratio of povidone/iodine (%wt/v) of at least 10.0 is effective for eliminating the microbial flora used in these examples.

EXAMPLE 18

An alginate hydrogel foam containing bacitracin was prepared as follows:
1. Component A was prepared by mixing 2.2 g of sodium alginate commercially available as "Protanal LF 20/60 Sodium Alginate" from Protan Inc. of North Hampton, New Hampshire, with 0.90 g of sodium carbonate and 38.4 g of deionized water, at room temperature The mixture was stirred until completely homogenous. Then 0.90 g of calcium carbonate was added with thorough mixing
2. Component B was prepared by mixing 5.0 g of bacitracin, USP, 50,000 units, commercially available from Pfizer, Inc, New York, NY, with 33.4 g of deionized water at room temperature. The mixture was stirred until completely dissolved. Then 2.2 g of glacial acetic acid was added with thorough mixing. Next 2.2 g of the same sodium alginate used in the preparation of Component A was added and the mixture was stirred until the alginate was completely dissolved.
3. Components A and B were loaded, in equal volumes, into separate barrels of a double-barreled mixing syringe assembly fitted with a 3-inch, 6-turn mixing tip; and
4. Components A and B were discharged through the mixing tip of the mixing syringe into a 50 ml conical tube and allowed to foam and cure for 3 minutes.

EXAMPLES 19-26

Medicated alginate hydrogel foams were prepared by the same method and from the same reactants used in the preparation of the alginate hydrogel foam of Example 18. The preparation of the alginate hydrogel foams of Examples 19-26 differs from the preparation of the foam of Example only in the concentration of bacitracin used. The concentrations of bacitracin used to prepare the foams of Examples 19-26 are shown in Tables V and VI. The bacteriostatic and bacteriocidal capabilities of the medicated hydrogel foams were measured by determining the Zone of Inhibition of microorganism growth in agar as described in Examples 4-11. The results are recorded in Table V.

TABLE V

| Ex. No. | Bacitracin (units/ml) | Zone of Inhibition | | |
|---|---|---|---|---|
| | | S. epid | E. coli | P. aerug |
| 19 | 250 | + + | + | + |
| 20 | 500 | + + | + | + |
| 21 | 750 | + + + | + + | + + |
| 22 | 1000 | + + + | + + | + + |
| 23 | 5000 | + + + + | + + + | + + + |
| 24 | 10000 | + + + + | + + + + | + + + + |
| 25 | 25000 | + + + + + | + + + + | + + + + |
| 26 | 50000 | + + + + + | + + + + | + + + + |

Increasing the concentration of bacitracin in the foam results in a steady increase in the Zone of Inhibition.

The microorganism $Log_{10}$ reduction method as described in Examples 4-11 was used to determine the effectiveness of the medicated hydrogel foam for eliminating microbial flora commonly found in an operative field. The results are recorded in Table VI.

TABLE VI

| Ex. No. | Bacitracin (units/ml) | $Log_{10}$ Reduction after 3.5 Minutes | | |
|---|---|---|---|---|
| | | S. epid | E. coli | P. aerug |
| 19 | 250 | 1.0 | 1.0 | 1.0 |
| 20 | 500 | 1.0 | 1.0 | 1.0 |
| 21 | 750 | 1.0 | 1.0 | 1.0 |
| 22 | 1000 | 1.0 | 1.0 | 1.0 |
| 23 | 5000 | 1.0 | 1.0 | 1.0 |
| 24 | 10000 | 1.0 | 1.0 | 1.0 |
| 25 | 25000 | 1.0 | 2.0 | 1.0 |
| 26 | 50000 | 1.0 | 2.0 | 1.0 |

Increasing the concentration of bacitracin results in only a small decrease in the average number of colonies; therefore, foams with concentrations of bacitracin of at least 50,000 units would not be effective for eliminating the microbial flora within 3.5 minutes. However, a longer exposure time would be effective as indicated by the results of the Zone of Inhibition Method.

EXAMPLES 27-38

An alginate hydrogel foam was prepared as follows:
(1) Component A was prepared by combining sodium alginate (commercially available from Protan Inc. of North Hampton, New Hampshire, under the trade designation Protanal LF 20/60), sodium carbonate and deionized water; stirring the combination until homogeneous; and then adding calcium carbonate.
(2) Component B was prepared by combining the same sodium alginate used in the preparation of Component A with deionized water, at room temperature; stirring until the alginate was completely dissolved; and then adding acetic acid.

The amounts of calcium carbonate, sodium carbonate and acetic acid used in Components A and B are shown in Table VII. The units used are grams.
(3) Components A and B were loaded, in equal volumes, into separate barrels of a double-barreled mixing syringe assembly fitted with a 3-inch, 6-turn mixing tip; and
(4) Components A and B were discharged through the mixing tip of the mixing syringe into three vials of known and equal volume and allowed to foam and cure. The vials were filled to overflowing, and as soon as the foaming action subsided, any material exceeding the volume of the vials was removed.

TABLE VII

| Ex. No. | Water | Component A | | | Component B | | |
|---|---|---|---|---|---|---|---|
| | | Sodium Alginate | Sodium Carbonate | Calcium Carbonate | Water | Sodium Alginate | Acetic Acid |
| 27 | 84.0 | 3.8 | 1.9 | 0.5 | 80.0 | 3.8 | 2.4 |
| 28 | 84.0 | 3.8 | 1.9 | 0.5 | 80.0 | 3.8 | 3.0 |
| 29 | 84.0 | 3.8 | 1.9 | 0.5 | 80.0 | 3.8 | 3.6 |
| 30 | 84.0 | 3.8 | 1.9 | 1.0 | 80.0 | 3.8 | 2.7 |
| 31 | 84.0 | 3.8 | 1.9 | 1.0 | 80.0 | 3.8 | 3.3 |
| 32 | 84.0 | 3.8 | 1.9 | 1.0 | 80.0 | 3.8 | 4.2 |
| 33 | 84.0 | 3.8 | 1.9 | 2.0 | 80.0 | 3.8 | 3.3 |
| 34 | 84.0 | 3.8 | 1.9 | 2.0 | 80.0 | 3.8 | 4.2 |
| 35 | 84.0 | 3.8 | 1.9 | 2.0 | 80.0 | 3.8 | 4.9 |
| 36 | 84.0 | 3.8 | 1.9 | 2.0 | 80.0 | 3.8 | 2.5 |
| 37 | 84.0 | 3.8 | 1.9 | 2.0 | 80.0 | 3.8 | 1.7 |
| 38 | 84.0 | 3.8 | 0 | 1.3 | 80.0 | 3.8 | 1.7 |

The time required for the production of a cured hydrogel foam was measured for each sample of each of the examples. In this regard cure time represents the time elapsed between the mixing of Components A and B and the point at which no further changes in the tackiness of the foam were detectable by touch. The average cure times for the three samples of each of the hydrogel foams produced in Examples 27–38 are shown in Table VIII.

TABLE VIII

| Example No. | Cure Time (minutes) |
|---|---|
| 27 | 22.7 |
| 28 | 10.7 |
| 29 | 7.7 |
| 30 | 6.7 |
| 31 | 4.7 |
| 32 | 3.3 |
| 33 | 2.3 |
| 34 | 2.0 |
| 35 | 1.5 |
| 36 | 3.0 |
| 37 | 50.0[1] |
| 38 | 1.0 |

[1] cure time measurements terminated with hydrogel foam still in tacky state.

Particularly in medical applications minimizing the application time of the hydrogel is highly desired since this reduces nursing time and the inconvenience to the patient. However, the cure time of the hydrogel must be of sufficient duration to allow the hydrogel forming solution to be applied to the body prior to the gelling and foaming activity Preferably the hydrogel foam forms and cures in a period of from about 2 to 5 minutes.

As shown in Tables VII and VIII, the cure time can be regulated via the concentration of the acid in Component A and the amount of polyvalent metal salt suspended in Component B. Cure times decrease as the concentration of the acid in Component A is increased and as the amount of the polyvalent metal salt suspended in Component B is increased. While varying the amount of either reactant can be used to control the cure time, it is preferable to use the minimum amount of acid necessary and regulate the cure time via the amount of metal salt present, since excessive acidity may have undesirable effects on the tissue compatibility of the mixture. Accordingly, the composition of Example 36, which produced a cured hydrogel foam in 3.0 minutes, and which had the lowest acid concentration of any of the compositions producing cured hydrogel foams within the desired range of cure times, is preferred over the other compositions tested.

Additionally, the density of the hydrogel foams produced in Examples 27–37, and the absorbency of the hydrogel foams produced in Examples 27–36 and 38 were measured. These are recorded in Table IX. The recorded density and absorbency reflects the average for the three samples made in each example.

TABLE IX

| Example No. | Density (g/cm$_3$) | Absorbency (%) |
|---|---|---|
| 27 | 0.38 | 62 |
| 28 | 0.31 | 66 |
| 29 | 0.29 | 68 |
| 30 | 0.33 | 56 |
| 31 | 0.30 | 49 |
| 32 | 0.28 | 49 |
| 33 | 0.30 | 71 |
| 34 | 0.29 | 43 |
| 35 | 0.29 | 27 |
| 36 | 0.34 | 147 |
| 37 | 0.57 | — |
| 38 |  | 8 |

The density was calculated simply by removing the foam sample from the vial, weighing it and dividing the weight by the volume of the vial.

The absorbency was measured by immersing the foam samples in a 0.9 weight percent solution of sodium chloride in water. After 24 hours, the test samples were removed from the solution, the excess solution on the surface of the samples was removed by blotting, and the samples were weighed. The absorbencies recorded in Table IX reflect the weight of the saline solution absorbed as a percentage of the initial weight of the sample, and were calculated by dividing the difference in the weight of the sample before and after immersion in the saline solution by the initial weight of the sample.

The absorbency data recorded in Table IX demonstrates that the ability of the hydrogel foam to absorb saline fluids is related to the void volume of the foam. The low void volume foam of Example 38, prepared without sodium carbonate, had a much lower absorbency than the higher void volume foams prepared in Examples 27–36.

What is claimed is:

1. A water-insoluble polysaccharide hydrogel foam comprising:
    (a) about 0.02 to 60 percent by weight of one or more polysaccharides complexed with a di- or trivalent metal salt;
    (b) the gaseous reaction product of an effervescent compound and a biocompatible, water-soluble acid in a concentration sufficient to provide the cured hydrogel foam with a density of from about 0.1 to 1 g/cm$^3$; and
    (c) from about 50 to 98 percent by weight of an aqueous medium.

2. The water-insoluble polysaccharide hydrogel foam of claim 1 wherein said polysaccharide is selected from the group consisting of the water-soluble salts of alginic acid, pectic acid and hyaluronic acid; the water-soluble salts and esters of polyglucuronic acid, polymanuronic acid, polylygalacturonic acid and polyarabinic acid, and gum kappa-carrageenan.

3. The water-insoluble polysaccharide hydrogel foam of claim 1 wherein said salt is selected from the group consisting of calcium carbonate, calcium phosphate dibasic, barium carbonate and zinc carbonate.

4. The water-insoluble polysaccharide hydrogel foam of claim 1 wherein said effervescent compound is an alkali metal carbonate or bicarbonate.

5. The water-insoluble polysaccharide hydrogel foam of claim 1 wherein said acid is a monocarboxylic or polycarboxylic acid.

6. The water-insoluble polysaccharide hydrogel foam of claim 1 wherein said foam further comprises a medicament.

7. The water-insoluble polysaccharide hydrogel foam of claim 6 wherein said medicament is an antimicrobial present in a concentration of between about 0.001 and 10 percent by weight of said foam.

8. A two-part aqueous based composition which upon mixing will yield a water-insoluble polysaccharide hydrogel foam, comprising
    (a) a first liquid component comprising
        (1) an aqueous dispersion of a water-insoluble di-or trivalent metal salt capable of reacting with an acid to form a water-soluble metal salt, said di- or trivalent metal ion capable of complexing with pendant carboxylate groups on water-soluble polysaccharides to form water-insoluble polysaccharide hydrogels, and
        (2) an effervescent compound capable of effervescence upon reaction with an acid; and (b) a second liquid component comprising an aqueous solution of a water-soluble acid; wherein either or both said first liquid component and said second liquid component further comprises a water soluble polysaccharide having pendant carboxylate groups dissolved therein 9. The two-part aqueous based composition of claim 8 wherein either or both said first liquid component and said second liquid component further comprise a medicament dissolved or suspended therein.

10. The two-part aqueous based composition of claim 8, wherein said polysaccharide is selected from the group consisting of the water-soluble salts of pectic acid and hyaluronic acid; the water-soluble salts and esters of polyglucuronic acid, polymanuronic acid, polylygalacturonic acid and polyarabinic acid, and gum kappa-carrageenan.

11. A method of making a medicated water-insoluble polysaccharide hydrogel foam comprising the steps of mixing together
   (a) a first liquid component comprising
      (1) an aqueous dispersion of a water-insoluble di-or trivalent metal salt capable of reacting with an acid to form a water-soluble metal salt, said di-or trivalent metal ion capable of complexing with pendant carboxylate groups on water-soluble polysaccharides to form water-insoluble polysaccharide hydrogels, and
      (2) an effervescent compound capable of effervescent compound capable of
   (b) a second liquid component comprising an aqueous solution of a biocompatible, water-soluble acid; wherein either or both said first liquid component and said second liquid component further comprises a water soluble polysaccharide having pendant carboxylate groups and a medicament dissolved or suspended therein.

12. A method of making a medicated water-insoluble polysaccharide hydrogel foam comprising the steps of mixing together
   (a) a first liquid component comprising:
      (1) water;
      (2) a water-soluble polysaccharide having pendant carboxylate groups;
      (3) a water-insoluble di- or trivalent metal salt capable of reacting with an acid to form a water-soluble metal salt, said di- or trivalent metal ion capable of complexing with pendent carboxylate groups on said polysaccharide to form a water-insoluble polysaccharide hydrogel;
      (4) an effervescent compound which effervesces upon reaction with an acid; and
      (5) a medicament and
   (b) a second liquid component comprising an aqueous solution of a biocompatible water-soluble acid.

13. The method of claim 11 wherein water is present in said first and second liquid components in an amount sufficient to provide that said water-insoluble polysaccharide hydrogel foam is comprised of about 50 to 98 percent by weight water.

14. The method of claim 11 wherein said water-soluble polysaccharide is selected from the group consisting of the water soluble salts of alginic acid, pectic acid and hyaluronic acid; the water-soluble salts and esters of polyglucuronic acid, polymanuronic acid, polylygalacturonic acid and polyarabinic acid; and gum kappa-carrageenan.

15. The method of claim 11 wherein said water-insoluble di- or trivalent metal salt is selected from the group consisting of calcium carbonate, calcium phosphate dibasic, barium carbonate and zinc carbonate.

16. The method of claim 11 wherein said biocompatible, water-soluble acid is a monocarboxylic or polycarboxylic acid.

17. The method of claim 11 wherein said effervescent compound is an alkali metal carbonate or bicarbonate.

18. The method of claim 11 wherein said medicament is an antimicrobial selected from the group consisting of iodophors, iodine and bacitracin.

19. A foamed polysaccharide hydrogel preoperative preparation prepared according to the method of claim 11.

20. A foamed polysaccharide hydrogel preoperative preparation made by the process comprising the steps of:
   (a) mixing together, to form a composite liquid mixture, a first liquid component comprising:
      (1) an aqueous dispersion of a water-insoluble di-or trivalent metal salt capable of reacting with an acid to form a water-soluble metal salt, said di- or trivalent metal ion capable of complexing with pendant carboxylate groups on water-soluble polysaccharides to form water-insoluble polysaccharide hydrogels, and
      (2) an effervescent compound capable of effervescence upon reaction with an acid; and a second liquid component comprising an aqueous solution of a biocompatible, water-soluble acid; wherein either said first or second liquid component further comprises a water soluble polysaccharide having pendant carboxylate groups and a medicament dissolved or suspended therein;
   (b) applying said composite liquid mixture to a surgical site;
   (c) allowing said composite liquid mixture to react to form a water-insoluble polysaccharide hydrogel foam.

21. A two-part aqueous based composition for preoperative preparations comprising
   (a) a first liquid component comprising:
      (1) water
      (2) a water-soluble polysaccharide having pendant carboxylate groups;
      (3) a water-insoluble di- or trivalent metal salt capable of reacting with an acid to form a water-soluble metal salt, said di- or trivalent metal ion capable of complexing with pendent carboxylate groups on said polysaccharide to form a water-insoluble polysaccharide hydrogel;
      (4) an effervescent compound which effervesces upon reaction with an acid; and
      (5) an antimicrobial; and
   (b) a second liquid component comprising an aqueous solution of a biocompatible water-soluble acid.

22. A foamed preoperative preparation comprising:
   (a) about 0.02 to 60 percent by weight of one or more polysaccharides complexed with a di- or trivalent metal salt;
   (b) the gaseous reaction product of an effervescent compound and a biocompatible, water-soluble acid in a concentration sufficient to provide the cured hydrogel foam with a density of from about 0.1 to 1 $g/cm^3$;
   (c) about 0.001 to 10 percent by weight of an antimicrobial; and (d) from about 50 to 98 percent by weight water.

23. A device useful for forming a water-insoluble polysaccharide hydrogel foam comprising:

(a) a first chamber containing a first liquid component comprising:
 (1) water;
 (2) a water-insoluble di- or trivalent metal salt capable of reacting with an acid to form a water-soluble metal salt, said di- or trivalent metal ion capable of complexing with pendant carboxylate groups on water-soluble polysaccharides to form water-insoluble polysaccharide hydrogels, and
 (3) an effervescent compound capable of effervescence upon reaction with an acid; and
(b) a second chamber containing a second liquid component comprising an aqueous solution of a biocompatible, water-soluble acid;
(c) means connected to said first and second chambers for allowing intermixing of said first liquid component and said second liquid component;
(d) an outlet in said device capable of allowing discharge of the mixture of said first liquid component and said second liquid component; wherein either or both said first liquid component and said second liquid component further comprises a water-soluble polysaccharide having pendant carboxylate groups and a medicament dissolved or suspended therein;

24. The device of claim 23 wherein said first and second chambers each include a discharge opening leading to a mixing chamber for mixing said first liquid component with said second liquid component.

25. The device of claim 23 wherein said first and second chambers are double-barreleds of a syringe and each barrel includes a plunger capable of forcing liquid from the barrel.

* * * * *

UNITED STATES PATENT AND TRADEMARK OFFICE
CERTIFICATE OF CORRECTION

PATENT NO. : 5,089,606

DATED : February 18, 1992

INVENTOR(S) : Susan M. Cole, James E. Garbe and Lewis P. Woodson

It is certified that error appears in the above-indentified patent and that said Letters Patent is hereby corrected as shown below:

Col. 1, lines 12-13, "waterin-soluble" should read --water insoluble--.

Col. 1, line 42, "gelatin" should read --gelation--.

Col. 1, line 68, "gelatin" should read --gelation--.

Col. 2, line 13, "gelatin" should read --gelation--.

Col. 2, line 50, "gelatin" should read --gelation--.

Col. 10, line 6, delete the "r" between "accomplishing" and "this".

Col. 10, line 48, "CaCO:" should read --$CaCO_3$--.

Col. 11, line 66, "rypticase" should read --Trypticase--.

Col. 14, line 4, "Examples 13-18" should read --Examples 13-17--.

Col. 15, line 21, "Example only" should read --Example 18 only--.

UNITED STATES PATENT AND TRADEMARK OFFICE
CERTIFICATE OF CORRECTION

PATENT NO. : 5,089,606
DATED : February 18, 1992
INVENTOR(S) : Susan M. Cole, et al It is certified that error appears in the above-indentified patent and that said Letters Patent is hereby corrected as shown below:

Col. 19, lines 30-31, after "effervescent compound capable of" should read effervescence upon reaction with an acid; and--.

Signed and Sealed this

Eighteenth Day of October, 1994

Attest:

BRUCE LEHMAN

Attesting Officer

Commissioner of Patents and Trademarks